United States Patent
Burr et al.

[19]

[11] Patent Number: 6,079,836
[45] Date of Patent: Jun. 27, 2000

[54] FLOW CYTOMETER DROPLET BREAK-OFF LOCATION ADJUSTMENT MECHANISM

[75] Inventors: Robert Burr, Miami; Todd Lary, Homestead; Erich Frazier, Weston; Osvaldo E. Miranda, Jr., Miami, all of Fla.

[73] Assignee: Coulter International Corp., Miami, Fla.

[21] Appl. No.: 09/119,368

[22] Filed: Jul. 20, 1998

[51] Int. Cl.[7] .................................................. G01N 33/28
[52] U.S. Cl. ........................... 357/70; 357/441; 357/335; 357/72; 357/73
[58] Field of Search ................................ 356/39, 70, 441, 356/335, 72, 73

[56] References Cited

U.S. PATENT DOCUMENTS

| | | |
|---|---|---|
| 3,710,933 | 1/1973 | Fulwyler et al. . |
| 3,761,941 | 9/1973 | Robertson . |
| 3,826,364 | 7/1974 | Bonner et al. . |
| 3,836,912 | 9/1974 | Ghougasian et al. . |
| 3,878,519 | 4/1975 | Eaton . |
| 3,953,860 | 4/1976 | Fujimoto et al. . |
| 3,963,606 | 6/1976 | Hogg . |
| 3,982,251 | 9/1976 | Hochberg . |
| 4,025,926 | 5/1977 | Fujimoto et al. . |
| 4,045,770 | 8/1977 | Arnold et al. . |
| 4,047,143 | 9/1977 | Burden et al. . |
| 4,325,483 | 4/1982 | Lombardo et al. . |

*Primary Examiner*—Frank G. Font
*Assistant Examiner*—Reginald A. Ratliff
*Attorney, Agent, or Firm*—Charles E. Wands; Mitchell E. Alter

[57] ABSTRACT

A droplet travel path monitoring mechanism for a flow cytometer is operative to adjust the droplet break-off point back to an initially calibrated spatial location, in the event of the departure from calibrated timing of gaps in the unsorted fluid droplet stream that have been created by the deflection of charged droplets. In addition, the flow cytometer is operative to monitor prescribed characteristics of deflected droplet streams, and to controllably adjust drop-sorting deflection parameters, so as to maintain the deflected travel path of sorted droplets coincident with the opening into a sorted droplet collection container, thereby maximizing collection of all sorted droplets.

20 Claims, 12 Drawing Sheets

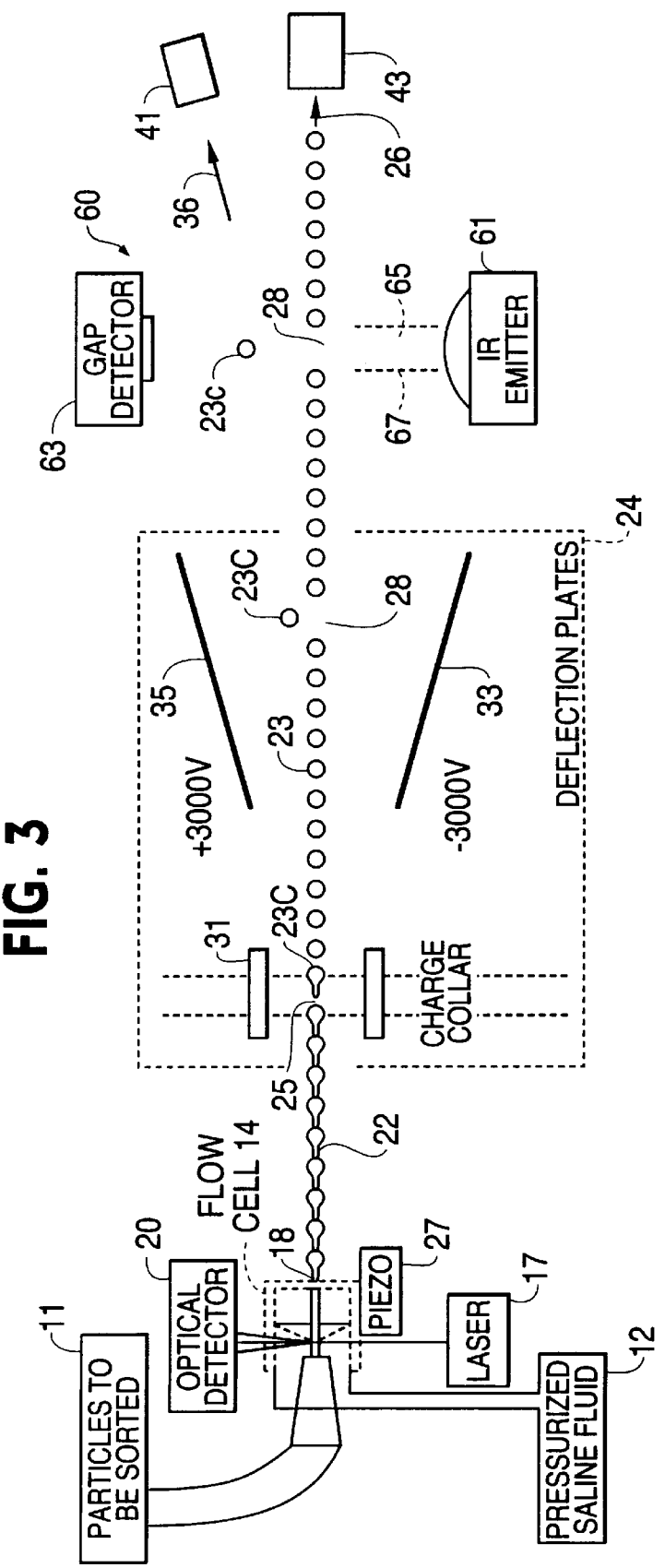

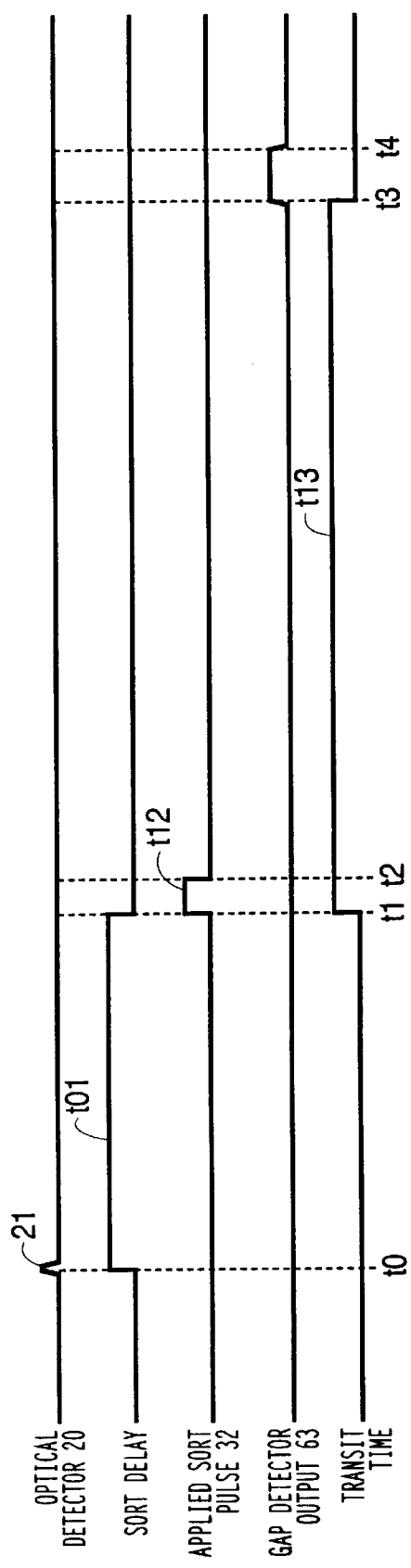

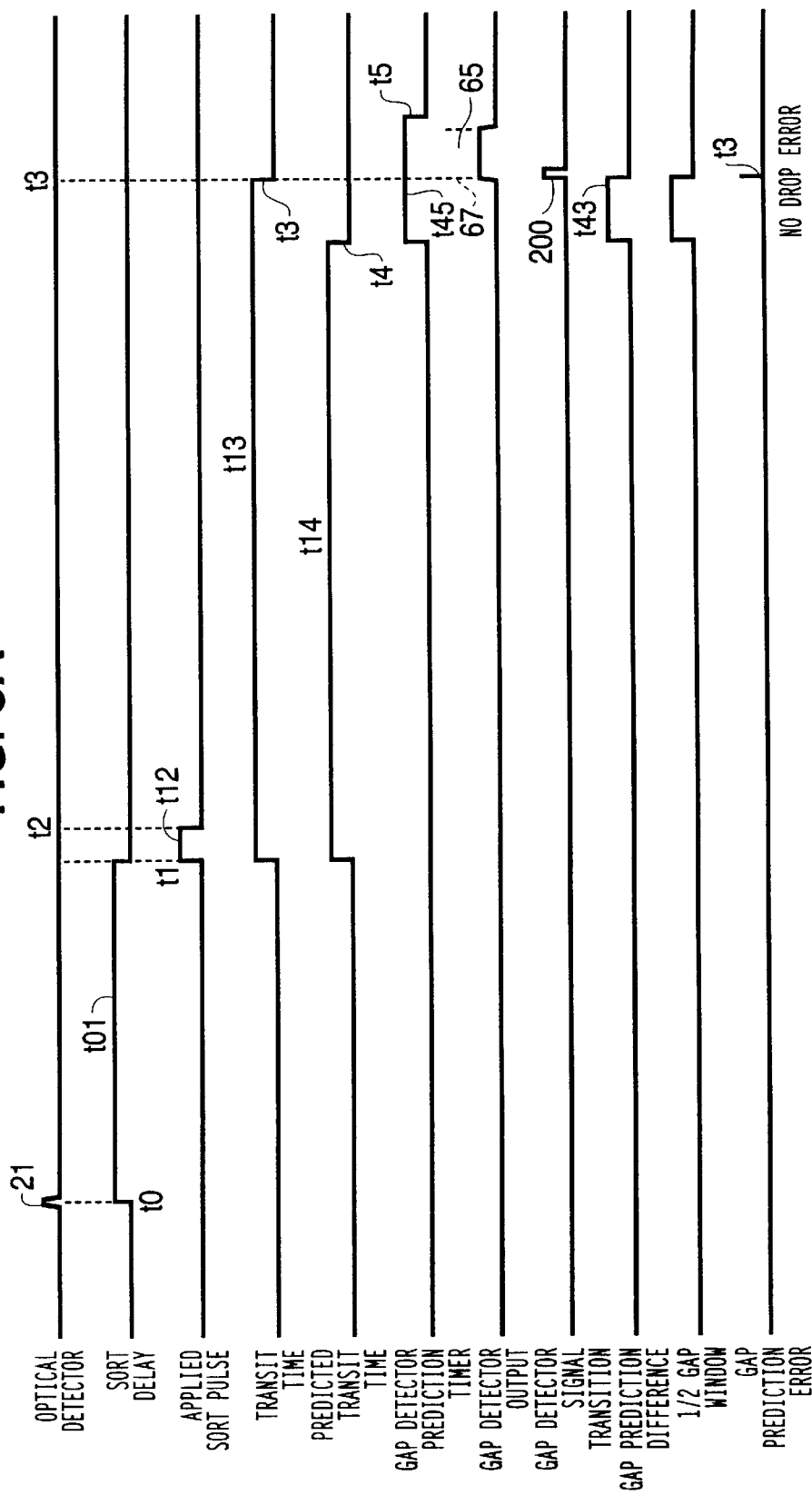

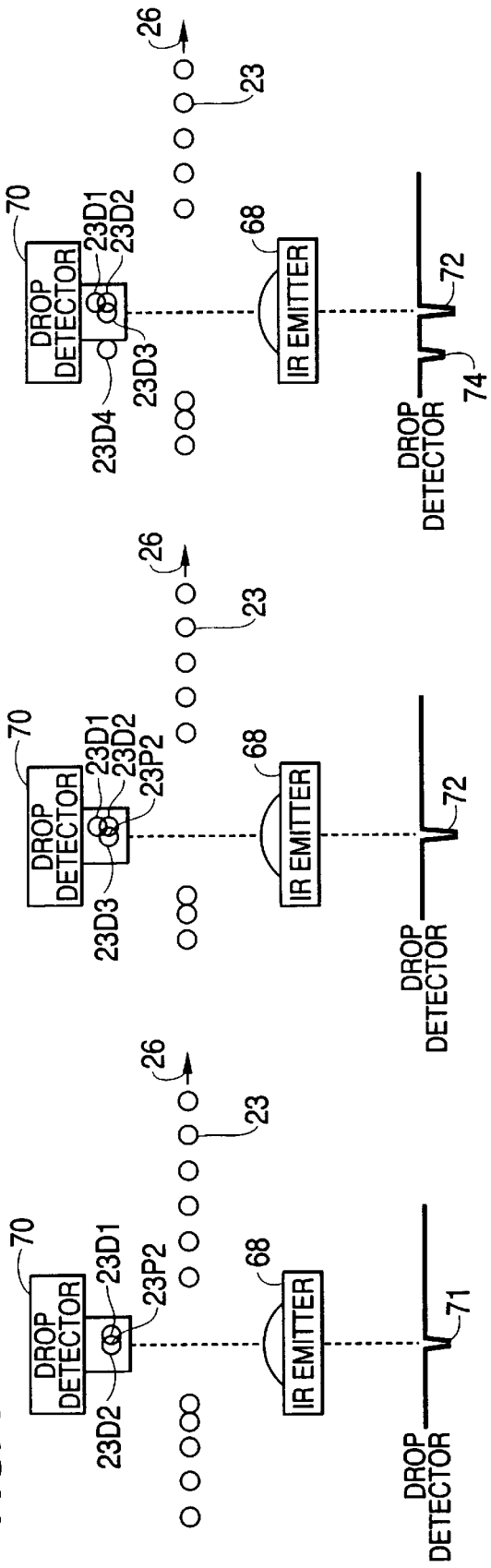

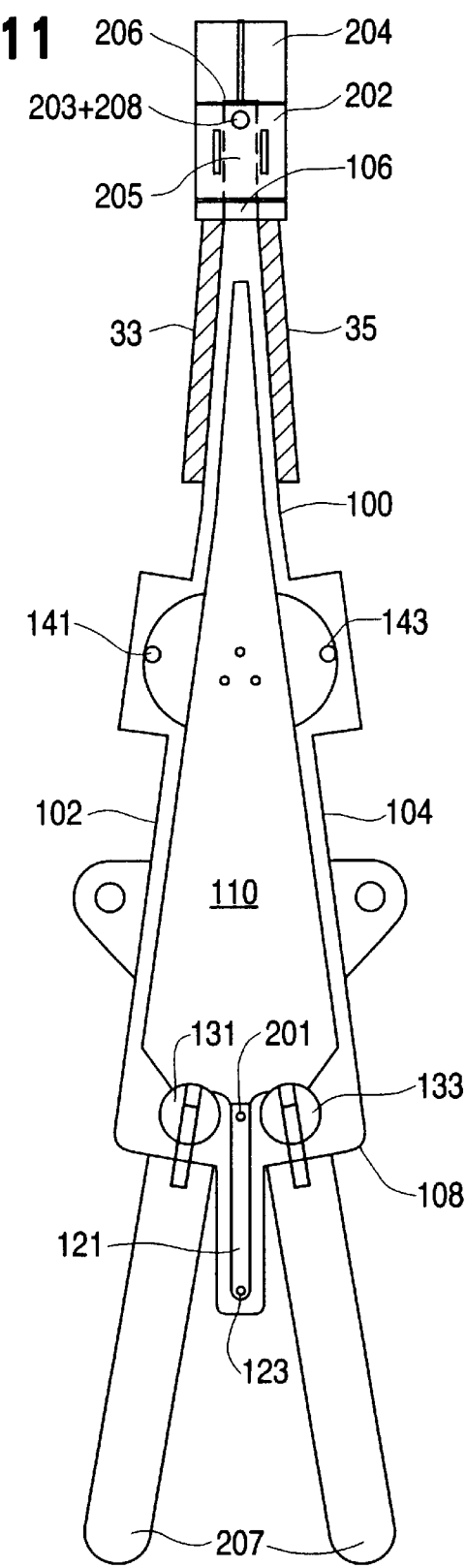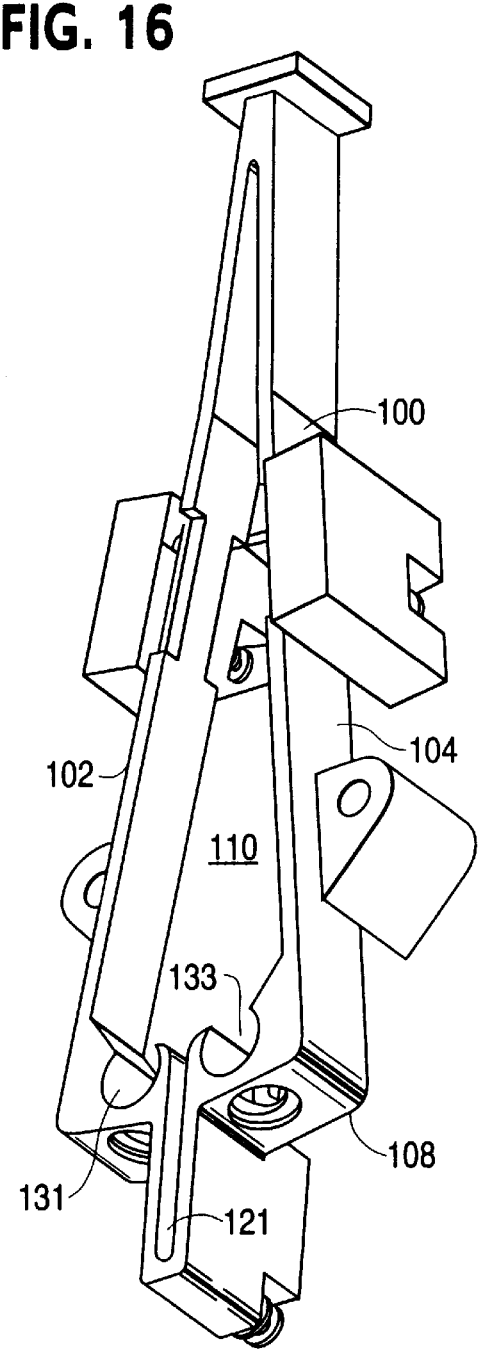

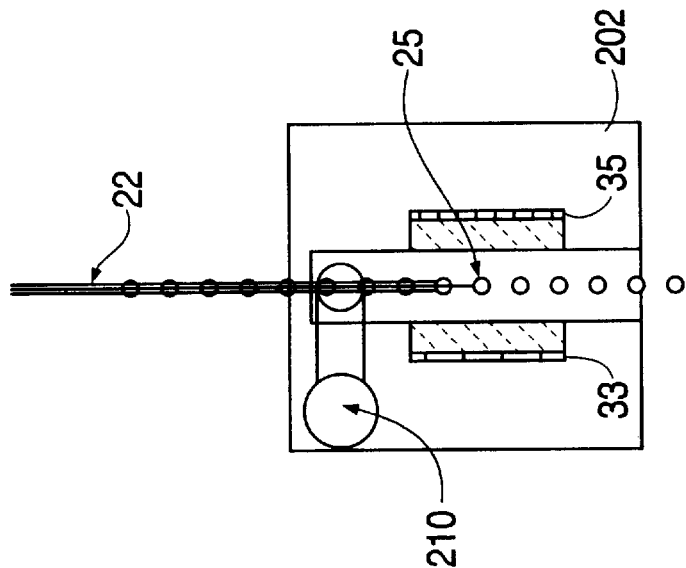
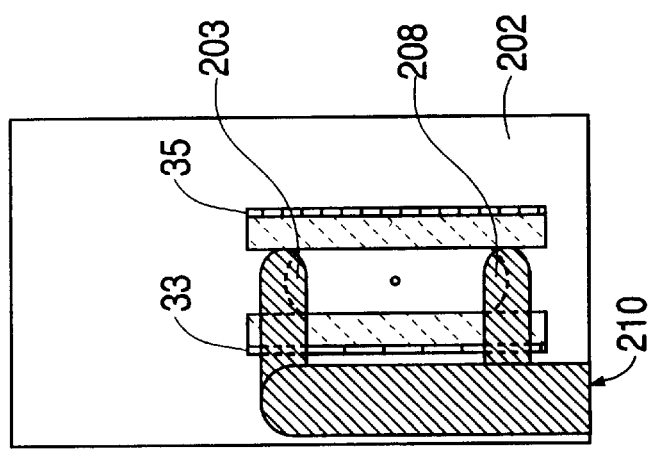
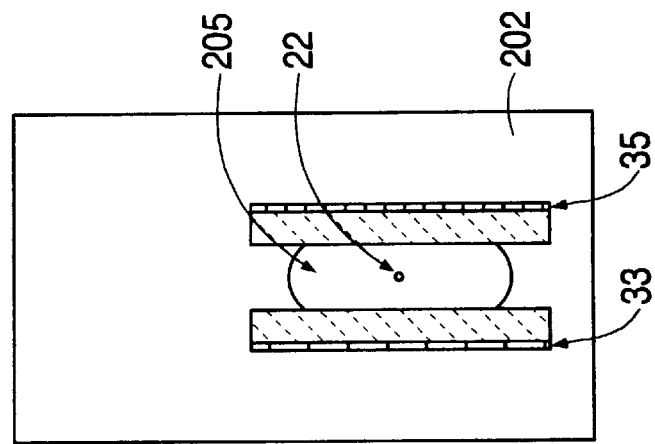

FLOW CYTOMETER DROPLET BREAK-OFF LOCATION ADJUSTMENT MECHANISM

FIELD OF THE INVENTION

The present invention relates in general to flow cytometer systems, and is particularly directed to a new and improved flow cytometer architecture and signal processing control mechanism therefor, that is operative to monitor prescribed characteristics of non-sorted and deflected droplet streams, and to controllably adjust drop-formation and drop-sorting deflection parameters, so as to maintain the point at which droplets break off from the cytometer's fluid stream at a calibrated droplet break-off location.

BACKGROUND OF THE INVENTION

Flow cytometers are commonly employed in the medical industry to analyze particles in a patient's body fluid (e.g., blood cells) as an adjunct to the diagnosis and treatment of disease. As a non-limiting example, in the course of chemotherapy treatment, such instruments may be used to sort and collect healthy blood cells (stem cells) from a quantity of blood that has been removed from a patient's bone marrow prior to chemotherapy. Once a chemotherapy treatment session is completed, a collected quantity of these cells is then reinjected back into the patient, to facilitate migration and healthy blood cell reproduction.

For this purpose, as illustrated in the cytometer system diagram of FIG. 1, particles 11 to be analyzed, such as cells of a centrifuged blood sample stored in a container 11, are injected into a (pressurized) continuous or uninterrupted stream of carrier fluid (e.g., saline) 12. This carrier fluid stream is directed along a flow channel 13 of a fluid flow chamber or cell 14. The fluid flow channel 13 is intersected at a location 15 by an output beam 16 emitted by an optical illumination subsystem, such as one or more lasers 17. Located optically in the path of the laser output beam 16 after its being intercepted by the carrier fluid stream are one or more photodetectors of a photodetector subsystem 20. The photodetector subsystem 20 is positioned to receive light modulated by the contents of (particles/cells within) the fluid stream, including light reflected off a cell, the blocking of light by a cell, and a light emission from a fluorescent dye antibody attached to a cell.

In order to avoid confusion as to which photodetector output signal is representative of which illuminated cell, the fluid flow channel 13 through the cytometer flow chamber is configured and sized to pass the particles or cells only one cell at the time through the intersection location 15 with the laser's output beam 16. As a consequence, as shown in the timing diagram of FIG. 2, as output signals from the photodetector subsystem 20 are modulated by particles transported by the carrier fluid stream, each modulation signal, such as that shown at 21 and occurring at a time t0 in the timing diagram of FIG. 2, can be associated with an individual cell. If the output of the photodetector subsystem 20 satisfies prescribed 'sort' criteria associated with one or more parameters of a desired cell, it is used to control the sorting of a droplet 23 of carrier fluid containing that cell by an electrostatic droplet sorter 24 located downstream of an exit port or aperture 18 of the flow chamber.

The carrier fluid stream is converted into individual droplets by an acoustically (e.g., piezoelectric transducer) driven droplet generator 27, which is coupled to the fluid flow chamber. The individual droplets do not form immediately at the exit port 18 of the fluid flow chamber, but proceed as an interconnected droplet stream 22 and break off at a location 25 downstream of the chamber exit port. Also, there is a 'sort' delay or interval of time t01 between the time t0 that the cell passes through the laser beam intersection location 15 and a subsequent time t1 at which the last attached portion of the carrier fluid stream containing that cell actually physically separates from the carrier fluid stream as a distinct droplet 23 in a stream or sequence of droplets traveling along a vertical travel path 26.

The location 25 at which the droplets form downstream of the flow chamber exit port 18 is adjusted by varying the parameters of the droplet generator drive signal. The rate at which droplets are formed is governed by the frequency of the acoustic drive signal, and the droplets become synchronized with the frequency of the piezo vibration of the droplet generator 27. As a non-limiting example, the acoustic drive frequency applied to the droplet generator 27 may be on the order of from four to one hundred Khz, at a fluid pressure on the order of from three to seventy psi.

The photodetector output is typically digitized and then analyzed by a cell type mapping or identification algorithm executed by an associated supervisory control processor of the cytometer's control workstation 50. Based upon this analysis, the control processor supplies control signals to a charging and deflection control circuit 52 of the droplet sorter 24 to sort or abort the droplet.

In order to controllably sort an individual droplet 23 that breaks off or separates from the fluid stream exiting the flow chamber's outlet port 18, the droplet sorter 24 employs an electrostatic charging collar 31 surrounding the travel path 26 of the droplet sequence. Charging collar 31 may comprise a metallic cylinder that is located so as to surround the location along the droplet sequence travel path 26 where the individual droplets 23 separate from the fluid stream, and is typically several droplets in length. The charging collar 31 is positioned vertically downstream of the fluid chamber exit port 18 and upstream of an associated set of electrostatic (opposite polarity, high voltage) deflection plates 33 and 35 between which the stream of charged droplets 23 pass as they travel downwardly and are either sorted along a sort path 36 into a sorted droplet collection container 41, or allowed to pass unsorted along travel path 26 into an aborted or discarded waste container 43.

Under the control of the cell analysis and sorting routine executed by the system workstation 50, a prescribed charging voltage pulse 32 of a duration t12 is selectively applied to the charging collar 31 at time t1, i.e. at the end of the sort delay t01, and terminating at time t2 at the end of the pulse duration interval t12, thereby charging a droplet 23C that should contain the cell to be sorted. As the selectively charged droplet 23C passes between the two opposite polarity high voltage deflection plates 33 and 35, it is attracted to the plate with the opposite charge, while being simultaneously repelled by the plate with the same or like charge. This electrostatic steering action directs the charged droplet 23C along a deflected travel path 36 on one side of the main droplet travel path 26, and into the sorted droplet collection container 41.

As described above, for any given cell or particle interest within the fluid stream, there is a 'sort' delay between the time t0 at which the photodetector subsystem 20 generates an output signal 21 for that cell and the time of the sorting pulse at which a droplet 23 containing that cell breaks off (at location 25) from the fluid stream.

Knowing the exact duration of this sort delay is critical to accurate sorting of the drops, since only the last attached droplet that breaks off from the fluid stream at the time t1 of the applied sort charging pulse 32 will be deflected by the deflection plates 33 and 35, and subsequently collected into the sorted droplet collection container 41.

Sort delay is affected by various parameters including the pressure of the carrier fluid, size and surface characteristics of the droplet generator exit port, the viscosity of the carrier fluid, and the amplitude of the piezo vibration. While some parameters, such as the pressure of the fluid carrier, which affect the position of the droplet formation point, can be controlled with precision, others cannot be controlled. For example, material may build up on the flow chamber exit port, causing a change in the natural energy of the fluid stream, and moving the droplet formation point closer to the flow chamber. Other factors include acoustic coupling of the instrument vibration, room noise, vibration in the room machinery external to the unit, and so on.

As a consequence, it is standard practice to conduct a preliminary set of test and calibration steps to accurately establish the droplet formation location 25. As a non-limiting example, this may be accomplished by initially manually setting the droplet formation point 25 at some predetermined distance from the laser intersection point 15, using a precision imaging aid (such as a microscope objective or a video camera) to observe the fluid steam. Strobing a light emitting diode in sync with the excitation frequency of the piezoelectric drive signal to the droplet generator 27 will make the droplets 23 formed from the fluid stream appear to be stationary. Then, by controllably increasing or decreasing the amplitude of the piezoelectric drive signal, the operator can move the droplet formation point closer or farther away from the laser intersection point, until the point at which the drops first form coincides with a reference or positioning mark.

Next, the operator inputs to the sorting system a sort delay time that has been determined on the basis of previous experimentation, so as to place the system within several drops of the actual sort delay time. In order to bring the system to within one droplet of accuracy, the operator sets up and runs a calibration sort operation, using test beads, which mimic biological cells in terms of size. The beads are sorted onto a slide, and the slide is observed (under a microscope) to determine whether the number of beads on the slide coincides with the number of beads the system reported as having sorted.

If the numbers do not coincide, then the system is adjusted by changing the sort delay time, or by moving the droplet formation point by varying the amplitude of the acoustic drive signal. This operation is iteratively repeated as necessary until the beads counts are correct. With the system thus initially calibrated, it may then be monitored visually for drift, with the operator observing the fluid stream and droplets for movement. To verify that the sort parameters remain the same, the slide and bead analysis sequence described above may be repeated. It will be readily appreciated that this trial and error procedure is a time consuming process, and sample may be lost or the sort container contaminated during the sorting process without operator knowledge.

Unfortunately, proposals that have been suggested to remedy the problem are complex and costly, and not necessarily complete solutions. For example, one proposal is to incorporate a test mode optical forward error correction system, comprised of an additional laser—photodetection subsystem, that takes a 'second look' into the continuous fluid stream at some point downstream of the laser beam intersection location 15, but prior to the droplet break off point 25. The purpose of the second optical system is to confirm that test beads that have been injected in the fluid stream arrive at the downstream detection location at a time that they are expected.

In accordance with another proposal, an auxiliary laser is employed to determine whether there has been a shift in the overall velocity of the droplet stream. An obvious shortcoming of this approach is that it does not address the fundamental problem of determining exactly where the last attached droplet breaks off from the fluid stream. A further proposal places a second laser at an initially established droplet break off point and then monitors the stream at that point. Unfortunately, since the laser is fixedly positioned, it cannot be readily repositioned if the break off point moves.

SUMMARY OF THE INVENTION

In accordance with the present invention, the above-discussed drawbacks of conventional flow cytometer instruments are successfully remedied by a feedback-based signal processing mechanism that is operative to maintain the droplet break-off point at an initially calibrated spatial location (within the droplet charge collar of a droplet sorting mechanism). As will be described, using an optical detector subsystem, the invention looks for gaps in the fluid droplet stream that have been created by the deflection of charged droplets. The difference between the times at which these gaps are detected at a prescribed downstream location in the path of the droplet stream and the times at which deflected droplets that created the gaps were charged at the droplet charge collar is compared with a calibration reference interval. Any difference between the two is employed to adjust the amplitude of the piezo drive signal to the droplet generator, as necessary, to bring the instrument back into calibration.

The instrumentation architecture of a flow cytometer system employing the droplet break-off location adjustment mechanism in accordance with the present invention augments the system of FIG. 1, described above, with an unsorted droplet 'gap' detector associated with the main or unsorted droplet travel path, and a deflected/sorted droplet detector associated with the sorted droplet travel path. The unsorted droplet gap detector comprises an optical energy source and an associated optical detector which are positioned to provide a viewing window that intersects the unsorted droplet travel path at a location downstream of the droplet sorter.

The unsorted droplet gap detector is operative to identify the presence of a gap in what is otherwise a generally spatially periodic sequence of unsorted (uncharged) droplets that have broken off from the carrier fluid stream at a location within the droplet sorter's charging collar and are traveling downwardly toward a waster container. The presence of a gap in the unsorted droplet stream indicates that a (to be sorted) droplet has been charged and is traveling along a deflection path toward a sorted droplet collection container.

In a properly calibrated system, the difference between the time at which a sorted/charged droplet breaks off from the fluid stream exiting the cytometer flow chamber and a subsequent time at which the gap in the droplet stream resulting from the deflection of the charged droplet arrives at the gap detector is a prescribed 'gap' transit time interval. As long as the system remains calibrated this gap transit time will remain constant. However, any change in the gap transit time will indicate that the droplet formation point has moved from its calibration point. The change in the gap transit time is employed to adjust the amplitude of the piezo drive signal to the droplet generator, so as to bring the instrument back into calibration.

In order to measure the travel time of a gap in the unsorted droplet stream, a 'predicted' gap transit timer is started at the termination of the sort delay, which is also coincident with the time at which a charging pulse is applied to the charging collar of the droplet sorter. The predicted gap transit timer is programmed to time out at a time which occurs prior to the time at which the gap is expected to arrive within the viewing window of the unsorted droplet gap detector. This time is set equal to the calibrated gap transit time interval, minus the length of time required for a droplet that is a prescribed number of (e.g., two) droplet locations upstream from the gap detector to reach the gap detector.

When the predicted gap transit timer times out, each of a gap detector prediction timer and a gap prediction difference timer is started. The gap detector prediction timer times out over a duration equal to some number N of droplet periods, which corresponds to the time required for N consecutive unsorted drops to travel past a given point along the unsorted droplet travel path. The time at which the gap detector prediction timer times out occurs slightly later than the time required for a droplet to travel from a position upstream of the gap detector's viewing window to a position downstream of that position, so that the gap detector prediction timer's timing window or interval is sufficient to cover a droplet travel distance that covers the entire width of the gap detector viewing window.

The gap prediction difference timer has a timing duration that begins at the end of the predicted gap transit timing window and terminates at the time at which the gap is detected by the unsorted droplet gap detector. Namely, the sum of the durations of the predicted gap transit window and the gap prediction difference window is equal to the calibrated gap transit time.

During the timing window of the gap detector prediction timer, the output of the gap-detector station's optical detector is monitored for a signal transition indicating the presence of a gap in the unsorted droplet steam. The occurrence of this gap detection signal at a time other than the expected (calibrated) time indicates a timing error, the value of which is equal to the measured value of the gap prediction difference timer minus the offset droplet periods.

A change in the gap transit time interval means that the droplet formation location has moved farther away (downstream) from or closer (upstream) to the exit port of the fluid flow chamber, and has caused a variation in the sort delay time interval. For this condition the amplitude of the piezo drive signal to the droplet generator is changed accordingly, so that droplets will break off at the calibrated point and thereby reduce the currently detected gap transit time interval into alignment with the calibrated interval.

Because the droplets travel through air between the exit port of the fluid flow chamber and the droplet collection containers, they encounter air resistance which affects the pattern of the droplets, and thereby interferes with gap timing. It has been observed that those droplets which have no droplets directly in front of them will encounter sufficient air resistance as to decrease their speed and cause them to fall back or be retarded slightly from their expected positions. However, it has also been found that droplets which have some number of droplets (e.g., three or more) directly in front of them will not encounter such air resistance, but will maintain their speed along their travel path. In order to compensate for this air-resistance gap-skewing problem, the gap measurements derived by the various timers for droplets traveling along the unsorted droplet travel path are not employed unless the gaps are immediately preceded by a prescribed number of non-sorted droplets (e.g., three or more).

In addition to affecting the travel of gaps along the unsorted droplet travel path, air resistance also retards the travel of deflected droplets along the sorted droplet deflection path. Although this air resistance is not a problem along the sorted travel path if the droplets being deflected/sorted are spaced apart from one another by undeflected droplets, it becomes a problem if the droplets being deflected from the unsorted travel path are immediately consecutive to one another.

Where two immediately consecutive droplets are deflected from the main travel path, the speed of the forwardmost droplet is retarded by the encountered air resistance, causing it to form a droplet pair or packet with the next consecutive and faster moving deflected droplet. When this droplet packet passes the sorted droplet detector, the detector sees what appears to be a single large droplet and therefore generates a single output pulse having an amplitude that is larger than in the case of a single droplet. The sorted droplet detector is employed to control the magnitude of the charging voltage pulse applied to the charging collar of the droplet sorter, so that the travel path of the sorted droplet will remain coincident with a droplet receiving opening into the sorted droplet collection container.

Where three immediately consecutive droplets are deflected from the main travel path, the resistance of the air retards the speed of the first two droplets so that they form a droplet trio packet with the next consecutive and faster moving third deflected droplet. When this droplet trio packet passes the sorted droplet detector, the droplet detector again sees what appears to be a single large droplet and therefore generates a single pulse having an amplitude that is larger than in the case of a single droplet or a droplet pair.

Where more than three consecutive droplets are deflected however, the fourth and any additionally consecutive droplets will not be effectively retarded by air resistance. It has been observed that where a droplet is preceded by three or more droplets, it travels unretarded and is spaced apart from an upstream droplet or packet of droplets. As a consequence, for more than three consecutive sorted droplets, the sorted droplet detector will detect an initial trio packet as a single large droplet followed by the fourth and any subsequent droplets as normal sized, individual droplets.

Because the output pulses from the sorted droplet detector are not discriminated as to size, each output pulse is seen to represent only one deflected droplet. To correct for the effect of the air resistance 'packetizing' of pairs and trios of droplets on the pulses generated by the sorted droplet detector, a determination is made as to whether the sort (droplet-charging) signals that are incrementally applied to the droplet sorter are associated with sequential droplets. If only two sequential sorting signals are generated, they are counted as a single droplet packet. If three or more sequential sorting signals are generated, the first three sort signals are counted as a single droplet packet, and any additionally consecutive sorting signals are counted as additional droplet packets.

These sorting signals are counted by a sorting signal counter, the output of which is compared with a running count of the number of pulses produced by the sorted droplet detector. If the difference between the two count totals exceeds a prescribed error limit, the magnitude of the charging voltage pulse applied to the charging collar of the droplet sorter is adjusted until the two compared droplet count values are the same. At this point the magnitude of the charging voltage applied to the droplet sorter's charging collar will be the value that causes the deflection travel path of the sorted droplets to be coincident with the opening into the sorted droplet collection container, thereby maximizing collection of all sorted droplets. Should adjustment of the charging voltage fail to bring the droplet count value difference within tolerance, an alarm condition is declared, terminating the sorting process until the system is recalibrated.

In addition to the problem of retarded speed caused by the resistance of the air through which both sorted and non-sorted droplets fall, there is an ancillary problem of effects of unwanted air currents in the sorting area. Because the gap timing adjustment mechanism is sensitive to very small fluctuations in the ambient air around the droplets, a transparent protective chamber is used to isolate the droplet travel region between the fluid flow chamber and the collection containers from the movement of ambient air, such as may be caused by motion of a system operator in the vicinity of the cytometer.

Now although such an isolation chamber is effective to shield the droplet travel paths of the cytometer from the entry of potentially disturbing air currents from the surrounding ambient, a problem associated with the use of such an enclosed housing is the fact that small fluid particles created when the droplets are formed may deposit on the interior surfaces of the chamber and obstruct the sensing regions of the gap detector and the sorted droplet detector. In addition, the substantial saline humidity may reduce the electrostatic breakdown potential between the deflection plates of the droplet sorter. To solve these potential problems, a pair of vacuum-controlled air curtains are directed along the interior wall surfaces of the isolation chamber. Because the air curtains flow only along the wall surfaces of the chamber, they do not interact with or affect the velocity or the direction of travel of the non-sorted or sorted droplets.

In rare circumstances in the course of a sorting operation, relatively long time intervals may occur between sorted droplets, during which output signals from the gap detector and the sorted droplet detector are unavailable for conducting the on-line system adjustments described above. To avoid having such droplet sorting inactivity prevent system adjustment, 'calibration' droplets, that have been determined to be devoid of any particles or cells of interest, are controllably charged at a reduced charging voltage (e.g., ten percent of nominal) applied to the charging collar of the droplet sorter. This reduced magnitude charge causes the selected empty droplets to be deflected along an auxiliary travel path off the unsorted droplet travel path but sufficiently spaced from the sorted droplet travel path, so that the calibration droplets cannot be collected by sorted droplet collection container.

Although this does allow the gap timing to be measured, it does not allow position of normally deflected droplets to be determined; if the deflection field voltage has degraded, the reduced charging voltage will not be sufficient to cause a detectable gap in the unsorted droplet stream, so that the deflection angle is verified as not having degraded.

In order to properly charge a droplet for deflection, the charging voltage pulse must be applied to the charging collar during the time that the droplet is still connected to or part of the fluid stream (as the last connected droplet), in order to ensure that a conductive path is available for charge transfer. Also, the charging voltage must be maintained until the droplet breaks off from the main fluid stream. The droplet will carry this charge until it comes in contact with a conductive surface, allowing the charge to dissipate off the droplet. The charging voltage pulse typically has a pulse width equal to one droplet period.

Pursuant to a further feature of the invention, the charging voltage pulse is terminated prior to the end of a normal droplet period, so as to ensure that a droplet being charged is still in the process of breaking off from the main carrier fluid stream at the calibrated sorting time. If the droplet break-off time drifts outside of this drop-charging window, then the droplet will be uncharged when it breaks off from the main carrier stream, so that it will not be deflected and leave a gap in the unsorted droplet stream. Although not sorting the droplet will be detected as a sorting error, the break-off location drift that caused the error will not allow an undesirable droplet to be charged and sorted), thereby avoiding contamination of the contents of the sorted droplet collection container.

BRIEF DESCRIPTION OF THE DRAWINGS

FIG. 3 diagrammatically illustrates the general instrumentation architecture of a flow cytometer system employing the droplet formation location adjustment mechanism in accordance with the present invention;

FIG. 4 is a timing diagram associated with the operation of FIG. 2;

FIGS. 5A and 5B are respective timing diagrams illustrating the manner in which the travel time of a gap in a droplet stream may be measured;

FIG. 7 diagrammatically illustrates two immediately consecutive deflected droplets forming a droplet pair packet;

FIG. 8 diagrammatically illustrates three immediately consecutive deflected droplets forming a droplet trio packet;

FIG. 9 shows four immediately consecutive deflected droplets forming a droplet trio packet followed by an individual droplet;

FIGS. 11, 12 and 13 diagrammatically illustrate an optically transparent air flow-constraining protective chamber;

FIG. 16 is a perspective view of the optically transparent air flow-constraining protective chamber of FIGS. 11–13;

FIGS. 17 and 18 are top views of a charging collar;

FIG. 19 is a front view of a charging collar; and

DETAILED DESCRIPTION

Figure 1:
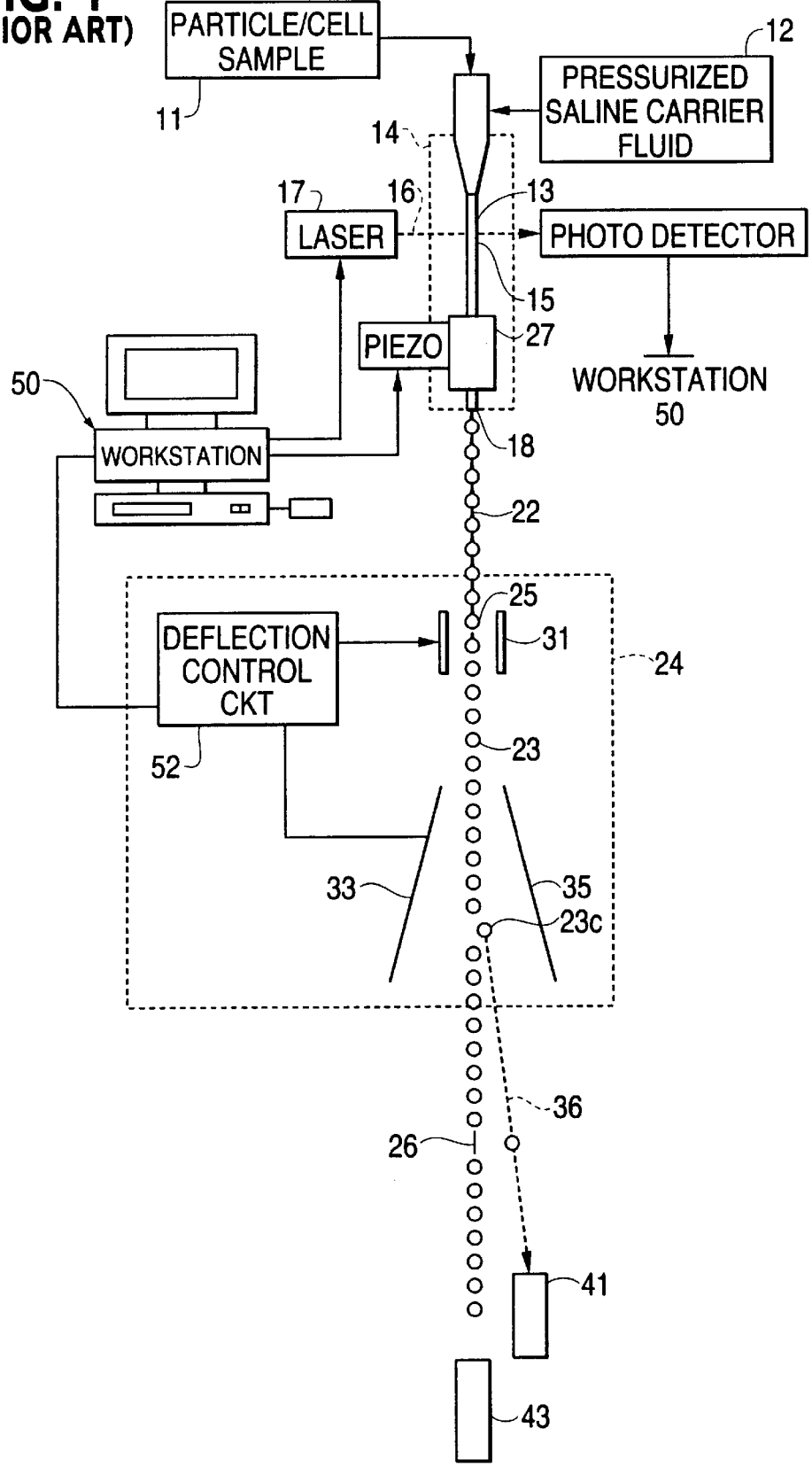
FIG. 1 diagrammatically illustrates the general instrumentation architecture of a flow cytometer.
Figure 2:
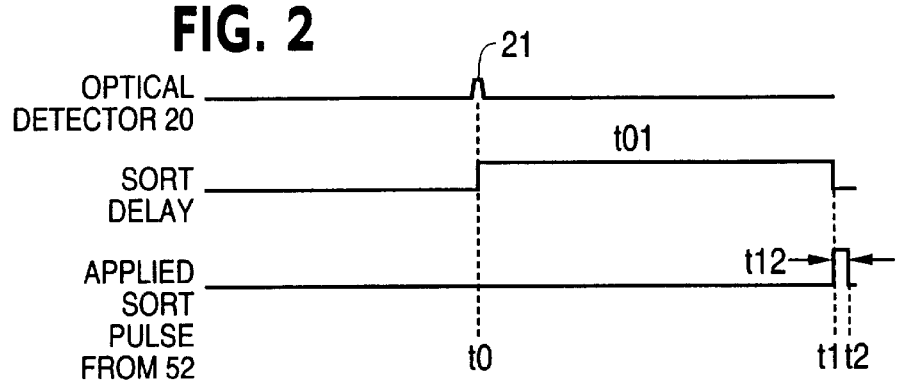
FIG. 2 is a timing diagram associated with the operation of FIG. 1.

Before describing in detail the new and improved flow cytometer droplet break-off location adjustment mechanism of the present invention, it should be observed that the invention resides primarily in what is effectively a prescribed arrangement of conventional flow cytometer instrumentation and associated digital signal processing components and attendant supervisory control circuitry therefor, that controls the operations of such circuits and components. Consequently, the configuration of such circuits components and the manner in which they are interfaced with other communication system equipment have, for the most part, been illustrated in the drawings by readily understandable block diagrams, which show only those specific details that are pertinent to the present invention, so as not to obscure the disclosure with details which will be readily apparent to those skilled in the art having the benefit of the description herein. Thus, the block diagram illustrations are primarily intended to show the major components of the flow cytometer system in a convenient functional grouping, whereby the present invention may be more readily understood.

FIG. 3 diagrammatically illustrates the instrumentation architecture of a flow cytometer system employing the droplet break-off location adjustment mechanism in accordance with the present invention, but rotated by 90°, in order to facilitate its association with respective timing diagrams, to be described. As shown therein the inventive cytometer architecture comprises essentially the same components as shown in FIG. 1, described above, but with an additional 'post-charging' droplet gap-monitoring station 60. This additional droplet gap-monitoring station is diagrammatically illustrated as comprising an optical energy source 61, such as an infrared emitter, and an associated optical detector 63, which are positioned to provide a viewing window 65 that intersects the droplet travel path 26 at a location downstream of the electrostatic deflection plates 33 and 35 of the droplet sorter 24.

As described briefly above, the function of the droplet gap-monitoring station 60 is to identify the presence of a gap 28 in what is otherwise a generally spatially periodic sequence of unsorted (uncharged) droplets 23 that have broken off from the carrier fluid stream 22 at a location 25 within the charging collar 31 and are traveling downwardly toward waste container 43. The presence of a gap 28 in the droplet stream indicates that a droplet has been charged and is traveling along deflection path 36 toward the sorted droplet collection container 41.

As shown in the timing diagram of FIG. 4, in a properly calibrated system, the difference between the time t1, at which a droplet charging pulse is applied to charge a droplet 23C as it breaks off from the fluid stream 22 at location 25 of the travel path, and the time t3, at which the gap 28 arrives at the droplet gap-monitoring station 60, is a prescribed 'gap' transit time interval t13. It is to be understood that the fluid pressure of the carrier stream is held constant by a separate fluid pressure control system (not shown), so that the velocity of the droplet stream does not change. As long as the system remains calibrated (namely, the point 25 at which the droplets break off from the fluid stream does not change) this gap transit time interval t13 will remain constant. However, any change in the length of the transit time interval t13 will indicate that the droplet formation point has changed from its calibration point.

For example, an increase in the gap transit time interval t13 means that the droplet formation location 25 has moved closer (upstream) to the exit port of the fluid flow chamber, and has thereby caused the drop (containing the particle which is qualified to be sorted) to break off from the fluid stream, before the sort pulse 31 is applied. This will cause the desired particle to travel to the waste container 43, instead of the collection container 41. If the time drifts by a whole drop, then the drop following will be sorted instead, which could contaminate the contents of the collection container 41 with whatever that droplet contained.

For this condition, the amplitude of the piezo drive signal to the droplet generator 27 is reduced, causing less vibrational energy to be coupled to the fluid stream, so that the droplets break off farther downstream, and bring the gap transit time interval t13 back into calibration. Conversely, a decrease in the gap transit time interval means that the droplet formation location 25 has moved farther away (downstream) from the exit port of the fluid flow chamber, and has caused the drop (containing the particle which is qualified to be sorted) to break off from the fluid stream, after the sort pulse 31 is applied. This will also cause the desired particle to travel to the waste container 43, instead of the collection container 41.

For this condition, the amplitude of the piezo drive signal to the droplet generator 27 is increased, causing more vibrational energy to be coupled to the fluid stream, so that droplets to break off farther upstream (closer to the fluid chamber's exit aperture), bringing the gap transit time interval back into calibration.

Figure 5B:
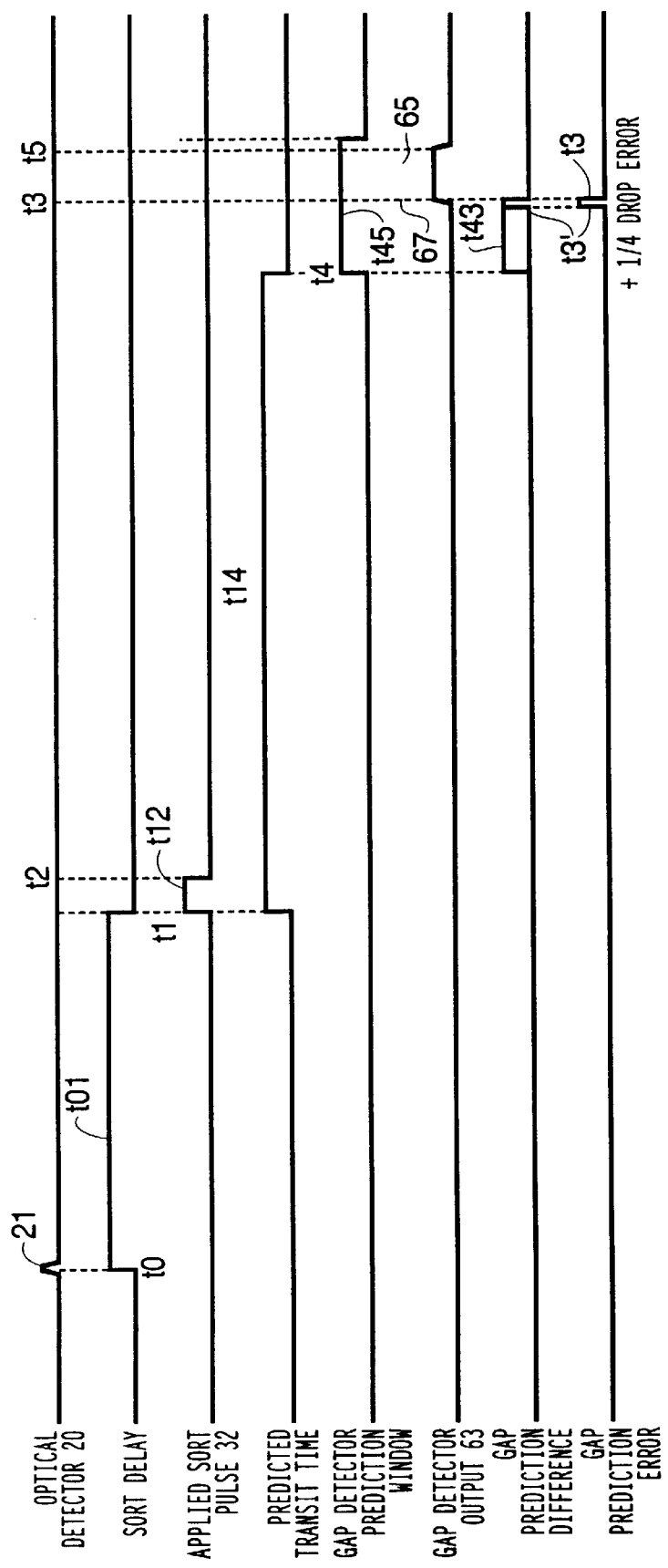

The manner in which the travel time of a gap in the droplet stream may be accurately measured is diagrammatically illustrated in the timing diagrams of FIGS. 5A and 5B. Although the following description will address the timing for an individually sorted droplet and its associated gap, it is to be understood that the various timing measurements of the processing sequence are carried out for all sorted droplets. This is accomplished by delaying all sort event signals by the transit time from the droplet sorter to downstream gap detection circuitry, and then comparing this delayed sort information with the signals from the gap detection and sorted droplet detection circuitry, as these signals are generated in real time.

For this purpose, as sort (drop charging) signals are applied to the droplet sorter 24, sort representative signals are written to sequential locations of a memory device at a rate equal to the resolution required for the sorting operation. As a non-limiting example, a write clock of 256 Khz, associated with a resolution of one-sixteenth of a droplet (when the piezo-electric transducer is driven at 16 KHz), may be employed.

The stored sorting data, which is to be compared with signals generated from downstream detection circuitry, is then read out of an offset location in the memory device, which corresponds to a delay of one transit period from the droplet sorter 24 to the detection circuitry. In this example, the transit time is divided by $1/256,000$ to determine the offset. In this manner, the delayed sorting information signals are effectively made concurrent with the real time detection signals from the gap and drop detectors. The data is then analyzed to determine if the events of interest are qualified, and the difference between the signals is written to memory for processing by the system processor.

More particularly, based upon a calibrated system, a predicted gap transit interval t14 is measured from the break-off/charging time t1 to time t4, which occurs prior to the time t3 at which the gap 28 is expected to arrive at the droplet gap-monitoring station 60. The time t4 at which the predicted gap transit timing window t14 terminates is set to be equal to the calibrated gap transit time interval t13, minus the length of time required for a droplet that is a predetermined number (e.g., two as a non-limiting example) of droplet locations upstream from the gap-monitoring station to reach the gap-monitoring station.

When the predicted gap transit interval t14 terminates at time t4, each of a gap detector prediction timing measurement interval t45 and a gap prediction difference timing measurement interval t43 is started. The gap detector prediction timing measurement interval t45 times out over a duration equal to some number N of droplet periods (e.g., four droplet periods), which corresponds to the time required for N (e.g., four) consecutive drops to travel past a given point along the droplet travel path 26.

Since the time t4, at which the predicted transit interval t14 terminates, is two droplets upstream of the front end 67 of the viewing window 65 of the gap-monitoring station 60, the time t5 at which the gap detector prediction timing measurement t45 times out is two droplet periods downstream of the upstream end 67 of the viewing window 65 of the gap-monitoring station 60. For the non-limiting example of FIGS. 5A and 5B, the time t5 occurs slightly later than the time required for a droplet to travel from a position two droplets upstream of the front end 67 of the viewing window 65 to a position four droplets downstream of that position, so that the timing window of gap detector prediction timing measurement t45 is sufficient to capture the actual gap as it passes the front end 67 of the viewing window 65, and to do so even if the gap has drifted by more than one drop.

The gap prediction difference timing measurement window t43 has a timing duration that begins at time t4 at the end of the predicted gap transit timing window t14 and terminates at the time at which the leading edge of gap 28 is detected at the droplet gap-monitoring station 60. Namely, the sum of the durations of the predicted gap transit timing window t14 and the gap prediction difference timing window t43 is equal to the actual gap transit time interval.

During the timing window of the gap detector prediction timing measurement t45, the output of the gap-detector station's optical detector 63 is monitored for a signal transition 200—indicating the presence of a gap in the droplet steam in travel path 26. FIG. 5A shows a gap transition with no error, where the gap occurs at time t3, which is the end of the calibrated transit time t13. To determine the error, one-half of the gap detector prediction timing window t45 is subtracted from the gap prediction difference t43, which in this case leaves zero, or no error.

However, as shown in the timing diagram of FIG. 5B, a gap detection signal may occur at time t3', which is earlier (e.g., by one droplet period), than the time t3 at which the gap signal should occur if the system were in calibration. In this case, the actual timing error (shown in FIG. 5B as a gap prediction error) is equal to the measured value of the gap prediction difference timing window t43 minus one-half of the gap detector prediction timer window, or two droplet periods.

As described above, a decrease in the gap transit time interval t13 means that the droplet formation location 25 has moved farther away (downstream) from the exit port of the fluid flow chamber, and has caused the plug of particle carrying fluid to become misaligned with the sort delay time, causing an uncertainty as to the location of the particle within a particular drop, thereby degrading the recovery of those particles in the sort collection container, as well as the purity.

For this condition where the gap detection time t3' occurs earlier than the calibrated gap detection time t3, the amplitude of the piezo drive signal to the droplet generator 27 will be slightly increased, so that droplets will break off farther upstream (closer to the fluid chamber's exit aperture), and thereby reduce the currently detected gap transit time interval t13' towards alignment with the calibrated interval t13.

Because the droplets travel through air between the exit port 18 of the fluid flow chamber 14 and the droplet collection containers 41 and 43, they encounter air resistance which affects the pattern of the droplets, and thereby interferes with gap timing. In particular, it has been observed that those droplets which have no droplets directly in front of them will encounter sufficient air resistance as to decrease their speed and cause them to fall back or be retarded slightly from their expected positions. However, it has been found that droplets which have some number of droplets (e.g., three or more) directly in front of them will not encounter such air resistance, but will maintain their speed along their travel path.

Figure 6:
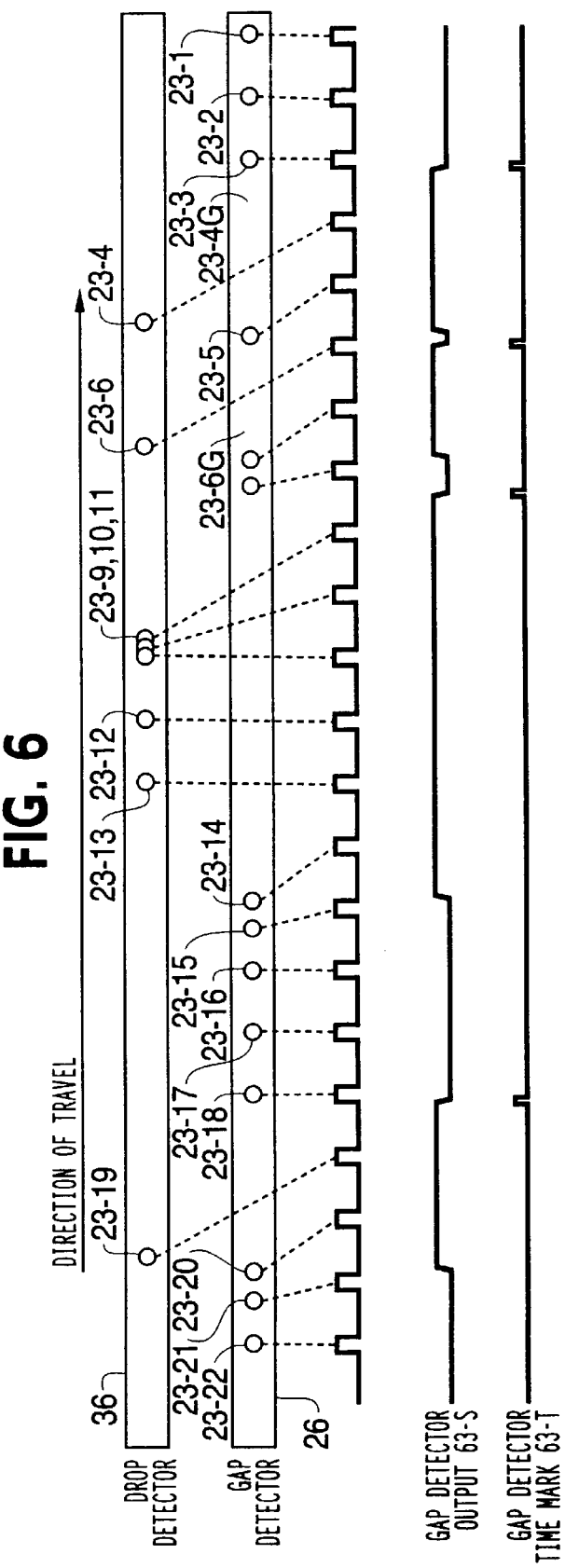
FIG. 6 diagrammatically illustrates the manner in which air resistance retards droplet travel speed.

This problem of encountered air resistance is illustrated diagrammatically in FIG. 6, wherein non-sorted droplets 23-1, 23-2 and 23-3 traveling along path 26 are followed by a gap 23-4G created by the sorting of a droplet 23-4 shown as traveling along the sorted droplet deflection path 36. Because of the presence of gap 23-4G directly ahead of non-sorted droplet 23-5, droplet 23-5 encounters air-resistance sufficient to retard its speed, shown in FIG. 6 as approximately one droplet period. The next droplet in the sequence is a sorted or deflected droplet 23-6 traveling along the deflection path 36, so that there is a gap 23-6G in the droplet travel path 26.

However, because the speed of the non-sorted droplet 23-5, which is immediately ahead of this gap 23-6G, has been retarded, the gap detection signal 63S supplied at the output of the gap-detector station's optical detector 63 and associated timing marks 63-T due to the presence of this gap will be inaccurate and cannot be used to adjust the droplet break-off location 25. A similar problem occurs for the gaps created by droplets 23-9 through 23-13. In the illustrated example, a useful gap does not occur again until droplet 23-19, which has five consecutive droplets 23-14 through 23-18 ahead of it. In order to compensate for the above-described air-resistance gap-skewing problem, the gap measurements derived by the various timing measurements for droplets traversing the main or unsorted droplet travel path 26 are not employed unless the gaps are immediately preceded by a prescribed number of non-sorted droplets (e.g., three or more).

In addition to affecting the travel of gaps along unsorted droplet travel path 26, air resistance also retards travel of deflected droplets along sorted droplet deflection path 36. This is not a problem if droplets deflected from unsorted droplet travel path 6 are spaced apart from one another by undeflected droplets (namely immediately consecutive droplets in the unsorted droplet travel path are not deflected). However, it is a problem if droplets deflected from unsorted droplet travel path 26 are immediately consecutive to one another.

More particularly, FIG. 7 diagrammatically illustrates the condition where two immediately consecutive droplets 23D1 and 23D2 are deflected from the unsorted droplet travel path. Because of the resistance of the air, the speed of the forwardmost droplet 23D1 is retarded, causing it to form a droplet pair packet 23P2 with the next consecutive and faster moving deflected droplet 23D2. When this droplet pair packet 23P2 intersects an optical beam generated by a light source 68, such as an IR emitter, the output of which is directed upon a deflected or sorted droplet detector 70, detector 70 sees what appears to be a single large droplet and therefore generates a single pulse 71 having an amplitude that is larger than the case of a single droplet. As will be described in detail below, sorted droplet detector 70 is employed to control the magnitude of the charging voltage pulse 32 applied to the charging collar 31, so that the travel path 36 of the sorted droplet will remain coincident with the opening into the sorted droplet collection container 41, thereby maximizing collection of all sorted droplets.

FIG. 8 diagrammatically illustrates the condition where three immediately consecutive droplets 23D1, 23D2 and 23D3 are deflected from the unsorted droplet travel path. Again, the resistance of the air retards the speed of the first two droplets 23D1 and 23D2, so that they form a droplet trio packet 23P3 with the next consecutive and faster moving deflected droplet 23D3. When this droplet trio packet 23P3 passes the sorted droplet detector 70, the droplet detector again sees what appears to be a single large droplet and therefore generates a single pulse 72 having an amplitude that is larger than the case of a single droplet or a droplet pair.

As pointed out above, the speed of a droplet having some number of droplets (e.g., three or more) directly in front of them will not be effectively retarded by air resistance. This effect for a deflected droplet is diagrammatically illustrated FIG. 9, which shows four immediately consecutive droplets 23D1–23D4 being deflected from the unsorted droplet travel path. Here, as in FIG. 8, the first three droplets 23D1–23D3 form a trio packet 23P3 that travel at the speed of the third droplet 23D3. However, because the fourth droplet 23D4 is preceded by three or more droplets, it travels unretarded and spaced apart from the trio packet 23P3. As a consequence, the sorted droplet detector 70 sees the trio packet 23P3 as a single large droplet followed by the fourth droplet 23D4, and therefore generates a first pulse 73 having a relatively large amplitude, followed by a second pulse 74 having an amplitude representative of a single droplet.

Because the output pulses from the sorted droplet detector 70 are not discriminated as to size, each output pulse is seen to represent only one deflected droplet. To correct for the effect of the air resistance 'packetizing' of pairs and trios of droplets on the pulses generated by the sorted droplet detector 70, a determination is made as to whether the sort (droplet-charging) signals that are incrementally applied to the droplet sorter 24 are associated with sequential droplets. If only two sequential sorting signals are generated, they are counted as a single droplet packet. If three or more sequential sorting signals are generated, the first three sort signals are counted as a single droplet packet, and any additionally consecutive sorting signals are counted as additional droplet packets.

Figure 10:
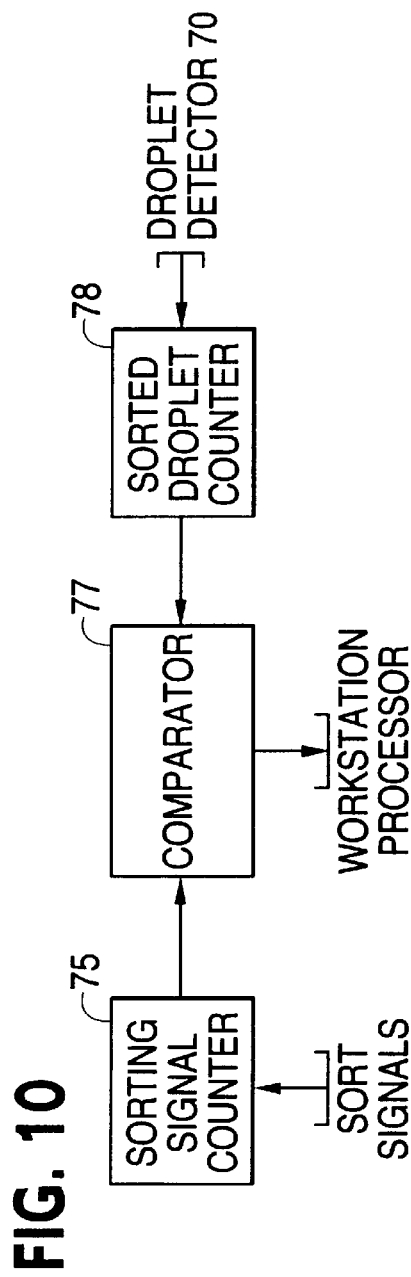
FIG. 10 diagrammatically illustrates the comparison of sorting signals counted by a sorting signal counter with droplet count signals.

As shown in FIG. 10, as these sorting signals are generated they are counted by a sorting signal counter 75, the output of which is compared in a comparator 77 with the output of a counter 78, which counts the pulses produced by the sorted droplet detector 70. If the difference between the two count totals exceeds a prescribed error limit, the magnitude of the charging voltage pulse 32 applied to the charging collar 31 of the droplet sorter 24 is adjusted by the workstation processor 50 until the two compared droplet count values are the same.

At this point, the magnitude of the charging voltage applied to the droplet sorter's charging collar will be the value that causes the deflection travel path 36 of the sorted droplets to be coincident with the opening into the sorted droplet collection container 41, thereby maximizing collection of all sorted droplets. If adjustment of the charging voltage fails to bring the droplet count value difference within tolerance, an alarm condition is declared, terminating the sorting process until the system is recalibrated.

In addition to the problem of retarded speed caused by the resistance of the air through which both sorted and non-sorted droplets fall, there is an ancillary problem of effects of unwanted air currents in the sorting area. In particular, the gap timing adjustment mechanism described above is sensitive to even very small fluctuations in movement of the ambient air around the droplets. Pursuant to a further feature of the present invention, this problem is effectively eliminated by confining the droplet travel region between the exit aperture 18 of the fluid flow chamber and the collection containers 41 and 43 within a protective isolation chamber.

In accordance with a preferred, but non-limiting embodiment, the protective chamber is optically transparent and may be configured in the manner shown in FIGS. 11–13 and 15–20, as a generally conically rectilinear housing 100 of a sturdy transparent material, such as a clear plastic material, having a pair of sidewalls 102 and 104, which diverge from an inlet port 106 and terminate at an endwall 108, so as to define an open interior region 110 therebetween. Top and bottom surfaces of the housing perimeter are covered by respective transparent cover plates 112 and 114. Attached with an air-tight seal to inlet port 106 of the chamber is the charging collar 202, and attached with an air-tight seal to the charging collar 202 is the flow cell 204. The charging collar 202 is configured as a cube-shaped plastic piece with a passage 205 through it, to allow the droplets exiting the flow cell 204 at orifice 206 to pass through to the chamber inlet 106.

The charged droplet deflection plates 33 and 35 are mounted alongside the exterior of sidewalls 102 and 104, as shown. The center of the endwall 108 has a generally longitudinal bore 121 that is aligned with the unsorted droplet travel path 26 and is coupled via an exhaust port 123 to waste collection container 43. In addition, a pair of sorted droplet collection ports 131 and 133 are disposed at portions of the endwall 108 offset to either side of the bore 121. The ports 131 and 133 are valved with stop-cocks to prevent contamination of the chamber by external unfiltered air, as well as to prevent biological material that may be left within the chamber after sorting hazardous particles from contaminating the instrument. These stop-cocks are closed by the operator when the collection tubes are removed. The sorted droplet collection container 207 is coupled to one of these droplet collection ports.

As described above, the use of an enclosed housing is subject to the fact that small fluid particles created when the droplets are formed may deposit on the interior surfaces of the chamber and obstruct the sensing regions of the gap detector and the sorted droplet detector. In addition, the substantial saline humidity may reduce the electrostatic breakdown or shorting potential between the deflection plates 33 and 35. These problems are effectively obviated by causing a pair of vacuum-controlled air curtains to flow along the interior wall surfaces of the chamber.

Figure 20:
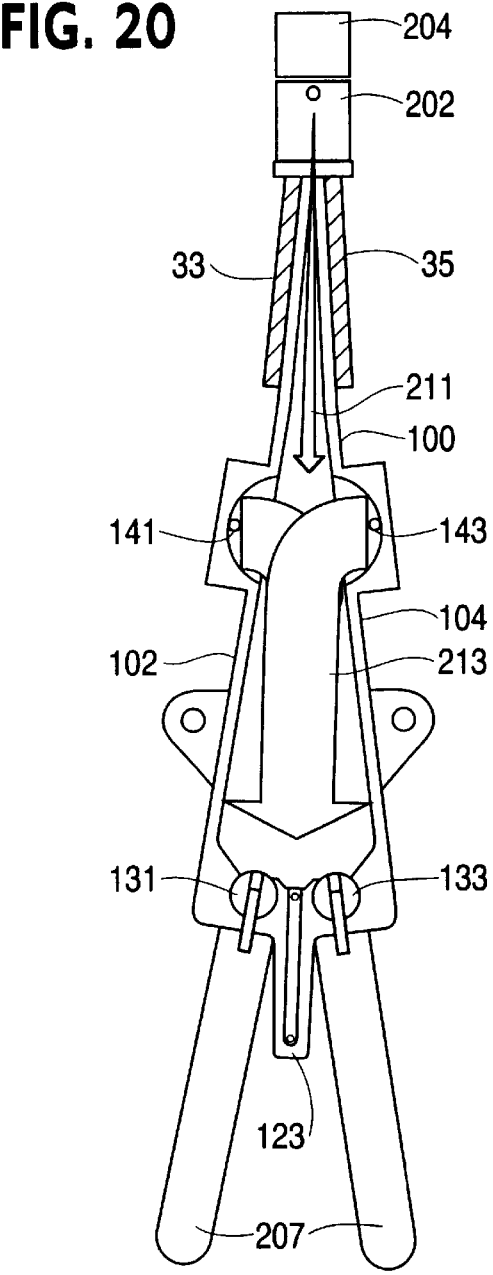
FIG. 20 diagrammatically illustrates air flow curtains within the optically transparent air flow-constraining protective chamber of FIG. 11.

For this purpose, as shown in FIGS. 11, 15, and 17–19, a pair of pneumatic inlet ports 203 and 208 in charging collar 202, which are coupled to an air inlet 210, as well as a pair of pneumatic inlet ports 141 and 143, are installed at sidewalls 102 and 104, so that, as shown in FIG. 20, vacuum-controlled air curtains 211, 213 are directed from the charging collar and from the ports 141, 143 along the interior wall surfaces of the isolation chamber.

To prevent bio-contamination of the chamber, and thus the sorted droplets, the chamber air inlet ports 141 and 143, as well as the charge collar inlet ports 203 and 208, are connected to filters designed to prevent the passage of particles two microns or larger. The filters are ported to the ambient air.

As pointed out above, because the air curtains flow only along the wall surfaces of the chamber, they do not interact with or affect the velocity or the direction of travel of the non-sorted or sorted droplets. The controlled air curtains are exhausted by way of low vacuum port 201. The vacuum level is set such that the air curtains are pulled through the chamber, but not so high that the air curtains interfere with the gap timing measurements. As a non-limiting example, a vacuum of one-half to one inch of mercury may be employed.

In some, albeit rare, circumstances during a sorting operation, relatively long time intervals may occur between sorted droplets, so that output signals from the gap detector 60 and the sorted droplet detector 70 are ostensibly unavailable for conducting the on-line system adjustments described above. To accommodate this possibility, the middle one of a trio of consecutive droplets, each of which has been determined to be devoid of any particles, is 'slightly' charged by applying a reduced magnitude voltage (e.g., one having only ten percent of the normal magnitude of the charging voltage pulse) to the charging collar 31.

Figure 14:
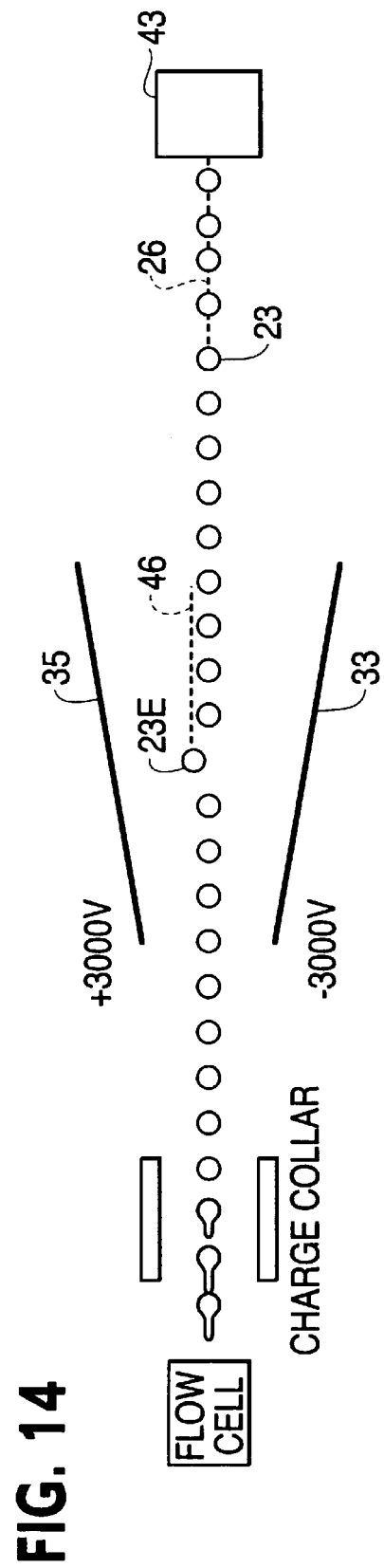
FIG. 14 diagrammatically illustrates the manner in which a reduced magnitude droplet charging pulse causes a selected empty droplet to be deflected along an auxiliary travel path.
Figure 12:
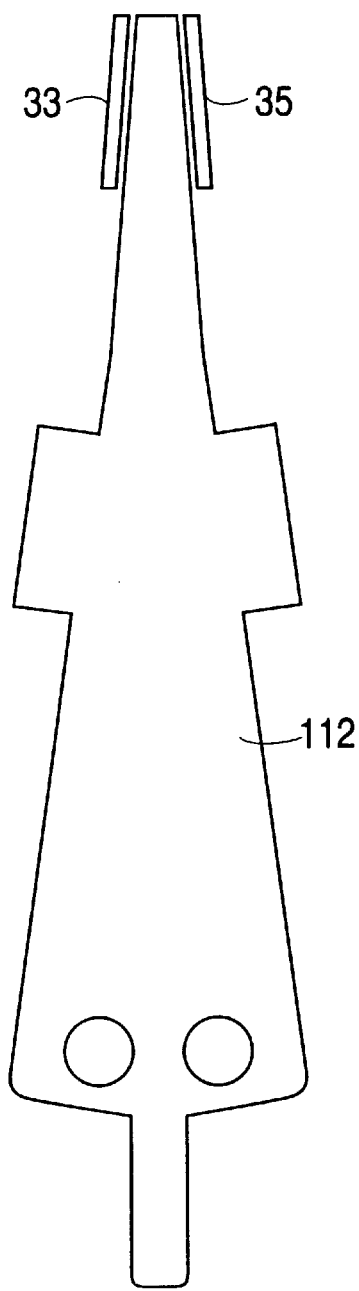
Figure 13:
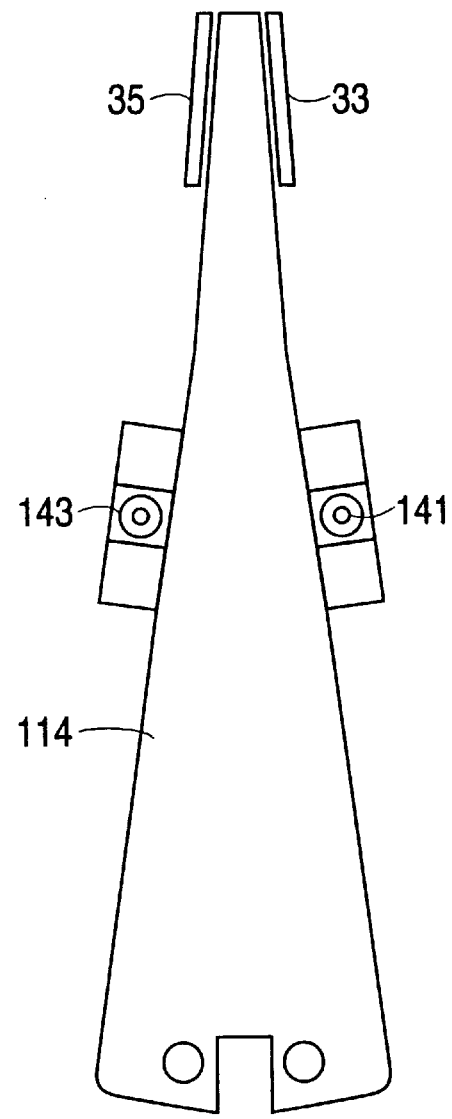
Figure 15:
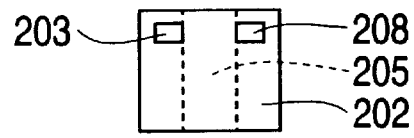
FIG. 15 shows a side view of a charging collar.

As diagrammatically illustrated in FIG. 14, this reduced magnitude charge causes the selected empty droplet 23E to be deflected along an auxiliary travel path 46, that is slightly off to the side of the unsorted droplet travel path 26, but still allowing the droplet 23E to be collected by the unsorted droplet collection container 43. This does not allow for checking the position of normally deflected droplets; however, if the deflection field voltage applied to plates 33 and 35 has degraded, the ten percent voltage will not be sufficient to cause a detectable gap 28 in the unsorted droplet stream, so that the deflection angle is verified as not having degraded.

In order to properly charge a droplet for deflection, the charging voltage pulse 32 must be applied to the charging collar 31, while the droplet is still connected to the fluid stream 22 (as the last connected droplet), in order to ensure that a conductive path is provided for charge transfer. In addition, the charging voltage must be maintained until the droplet breaks off from the fluid stream. The droplet will carry this charge until it comes in contact with a conductive surface, allowing the charge to dissipate off the droplet. The charging voltage pulse typically has a pulse width equal to one droplet period.

In accordance with a further feature of the invention, in order to ensure that a droplet being charged is still in the process of breaking off from the carrier fluid stream at the calibrated sorting time, the width of the charging voltage pulse 32 is reduced to some fraction of a normal droplet period (e.g., thirty percent, as a non-limiting example). If the droplet break-off time drifts outside of this drop-charging window, then the droplet will not have any charge when it breaks off from the carrier stream, so that it will not be deflected and leave a gap 28 in the unsorted droplet stream. Although the resultant failure to sort the droplet will be detected as an error by the comparator 77, the break-off location drift that caused the error will not allow an undesirable droplet to be charged (and thereby sorted), thereby avoiding contamination of the contents of the sorted droplet collection container 41.

As will be appreciated from the foregoing description, the above-discussed drawbacks of conventional flow cytometer calibration adjustment schemes are successfully remedied by the droplet travel path monitoring mechanism of the present invention, which is operative to adjust the droplet break-off point back to an initially calibrated spatial location, in the event of the departure from calibrated timing of gaps in the unsorted fluid droplet stream that have been created by the deflection of charged droplets. In addition, the invention is operative to monitor prescribed characteristics of deflected droplet streams, and to controllably adjust drop-sorting deflection parameters, so as to maintain the deflected travel path of sorted droplets coincident with the opening into a sorted droplet collection container, thereby maximizing collection of all sorted droplets.

While we have shown and described an embodiment in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed:

1. For use with a flow cytometer, wherein a carrier fluid flows along a channel coupled to a droplet generator that controls a point at which droplets break off from said carrier fluid, and a droplet sorter is operative to cause selected droplets to be charged and sorted along a sorted droplet deflection path, separate from an unsorted droplet path along which a stream of unsorted droplets travel, a method of controlling said point at which droplets break off from said carrier fluid, said method comprising the steps of:

(a) monitoring said unsorted droplet path for the presence of a gap in said unsorted stream of droplets created by the sorting of a droplet therefrom by said droplet sorter; and (b) controllably adjusting the operation of said droplet generator in accordance with detection of said gap in step (a).

2. A method according to claim 1, wherein step (b) comprises controllably adjusting the operation of said droplet generator in accordance with the difference between a first time interval, between the time at which said gap is detected and the time at which the sorted droplet that created said gap was charged, and a second, prescribed time interval.

3. A method according to claim 2, wherein step (a) comprises monitoring said unsorted droplet path by means of a gap detector for the presence of a gap in said unsorted stream of droplets created by the sorting of a droplet therefrom by said droplet sorter, and wherein step (b) comprises the steps of:

(b1) starting a predicted gap transit timer at the time at which said droplet sorter is caused to sort a droplet, (b2) terminating said predicted gap transit timer at a time prior to the time at which said gap is expected to be detected by said gap detector in step (a), minus a length of time required for a droplet that is a prescribed number of droplet periods upstream from said gap detector to reach said gap detector, (b3) in response to said predicted gap transit timer timing out in step (b2), starting a gap detector prediction timer and a gap prediction difference timer, said gap detector prediction timer timing out after a duration of a plurality of droplet periods that extend to a time later than the time required for a droplet to travel from a position upstream of said gap detector to a position downstream of that position, and wherein said gap prediction difference timer has a timing duration that begins upon said predicted gap transit timer timing out and terminates at the time at which said gap arrives at said gap detector, (b4) monitoring said gap detector during the timing period of said gap detector prediction timer for an output signal representative of a gap in said unsorted droplet steam, and (b5) in response to the occurrence of said output signal at a time other than said expected time, controllably adjusting the operation of said droplet generator.

4. A method according to claim 1, further including the step (c) of monitoring said sorted droplet deflection path for the presence of sorted droplets, and wherein step (b) comprises controllably adjusting the operation of said droplet sorter in accordance with detection of said sorted droplets in step (c).

5. A method according to claim 4, wherein step (c) comprises controllably adjusting the operation of said droplet sorter in accordance with a prescribed relationship between the number of sorted droplets detected in said sorted droplet deflection path and the number of droplets selectively sorted by said droplet sorter.

6. A method according to claim 1, wherein step (b) comprises controllably adjusting the operation of said droplet generator in response to a gap detected in step (a) satisfying a prescribed gap qualification criterion based upon at least one of resistance of air encountered by said stream of unsorted droplets travel, and the number of successive unsorted droplets immediately preceding a downstream end of said gap.

7. A method according to claim 1, further including the step (c) of shielding portions of said sorted droplet deflection path and said unsorted droplet path from fluctuations in ambient air around said cytometer by directing a fluid curtain along a wall surface of a transparent protective shroud.

8. A method according to claim 1, further including the step (c) of controllably charging selected droplets that have been determined to be devoid of particles at a reduced charge value, so as to cause said selected droplets to be deflected along an auxiliary travel path between said sorted droplet deflection path and said unsorted droplet path, and determining whether a deflection field voltage of said droplet sorter has degraded in accordance with whether or not a gap is detected in said unsorted droplet stream.

9. A flow cytometer having a fluid flow chamber having channel through which a carrier fluid flows, said channel being coupled to a droplet generator that controls a point along a carrier fluid travel path at which droplets break off from said carrier fluid, and a droplet sorter that is operative to cause selected droplets to be charged and sorted along a sorted droplet deflection path, separate from an unsorted droplet path along which a stream of unsorted droplets travel, a gap detector which is operative to monitor said unsorted droplet path for the presence of a gap in said unsorted stream of droplets created by the sorting of a droplet therefrom by said droplet sorter, and a controller which is operative to controllably adjust the operation of said droplet generator in accordance with detection of said gap by said gap detector.

10. A flow cytometer according to claim 9, further including a sorted droplet detector coupled to monitor said sorted droplet deflection path for the presence of sorted droplets, and wherein said controller is operative to controllably adjust the operation of said droplet sorter in accordance with detection of said sorted droplets by said sorted droplet detector.

11. A flow cytometer according to claim 10, wherein said controller is operative to controllably adjust the operation of said droplet sorter in accordance with a prescribed relationship between the number of sorted droplets detected in said sorted droplet deflection path and the number of droplets selectively sorted by said droplet sorter.

12. A flow cytometer according to claim 9, wherein said controller is operative to controllably adjust the operation of said droplet generator in response to a gap detected by said gap detector satisfying a prescribed gap qualification criterion, based upon at least one of resistance of air encountered by said stream of unsorted droplets travel, and the number of successive unsorted droplets immediately preceding a downstream end of said gap.

13. A flow cytometer according to claim 9, wherein said controller is operative to cause said droplet sorter to charge selected droplets that have been determined to be devoid of particles at a reduced charge value, so as to cause said selected droplets to be deflected along an auxiliary travel path between said sorted droplet deflection path and said unsorted droplet path, and determining whether a deflection field voltage of said droplet sorter has degraded in accordance with whether or not a gap is detected in said unsorted droplet stream.

14. A flow cytometer according to claim 9, wherein said controller is operative to adjust the operation of said droplet generator in accordance with the difference between a first time interval, between the time at which said gap is detected and the time at which the sorted droplet that created said gap was charged, and a second, prescribed time interval.

15. A flow cytometer according to claim 9, further including a protective chamber which is configured to shield portions of said sorted droplet deflection path and said unsorted droplet path from fluctuations in ambient air around said cytometer by directing a fluid curtain along an internal wall surface thereof.

16. A flow cytometer according to claim 15, wherein said protective chamber comprises an optically transparent, generally conically rectilinear housing having a pair of sidewalls, which diverge from an inlet port and terminate at an endwall, so as to define an open interior droplet travel region therebetween, and wherein a droplet charging collar is located at an upper neck portion of said protective chamber adjacent to said fluid flow chamber, and wherein charged droplet deflection plates are positioned alongside exterior sidewalls of said protective chamber.

17. A flow cytometer according to claim 16, further including a fluid inlet port at said upper neck portion of said protective chamber, and fluid inlet ports at said pair of sidewalls, which are operative to direct vacuum-controlled fluid curtains along interior wall surfaces to a pneumatic exhaust port of said chamber.

18. A protective chamber for a flow cytometer having a channel through which a carrier fluid flows, said channel being coupled to a droplet generator that controls a point at which droplets break off from said carrier fluid, and a droplet sorter which is operative to charge and sort selected droplets along a deflection path, separate from an unsorted droplet path along which unsorted droplets travel, said protective chamber comprising an optically transparent, generally conically rectilinear housing having a pair of sidewalls, which diverge from an inlet port and terminate at an endwall, so as to define an open interior droplet travel region therebetween, and wherein a droplet charging collar is located at an upper neck portion of said protective chamber adjacent to said fluid flow chamber, and wherein charged droplet deflection plates are positioned alongside exterior sidewalls of said protective chamber.

19. A protective chamber according to claim 18, further including a fluid inlet port at said upper neck portion of said protective chamber, and fluid inlet ports at said pair of sidewalls, which are operative to direct vacuum-controlled fluid curtains along interior wall surfaces to a pneumatic exhaust port of said chamber.

20. A protective chamber according to claim 19, wherein said endwall has a generally longitudinal bore aligned with said unsorted droplet path and being coupled by way of an exhaust port to a waste droplet container, and further including a plurality of sorted droplet collection ports disposed at portions of said endwall that are offset from said generally longitudinal bore, and having valves that prevent contamination of said interior droplet travel region therebetween by external unfiltered air, and prevent biological material within said chamber from contaminating said flow cytometer.

* * * * *